United States Patent [19]
Rajagopalan et al.

[11] Patent Number: 5,908,931
[45] Date of Patent: Jun. 1, 1999

[54] PREORGANIZED HEXADENTATE LIGANDS USEFUL IN RADIOGRAPHIC IMAGING AGENTS

[75] Inventors: Raghavan Rajagopalan, Maryland Heights; William L. Neumann, Grover; Dennis L. Nosco, Florissant, all of Mo.

[73] Assignee: Mallinckrodt Inc., St. Louis, Mo.

[21] Appl. No.: 07/627,175

[22] Filed: Dec. 14, 1990

[51] Int. Cl.$^6$ .................. C07F 9/80; C07F 9/06; C07D 221/16; C07D 221/02
[52] U.S. Cl. .............. 546/3; 546/264; 546/266; 546/267; 546/268.1; 546/312; 546/304; 546/329; 546/4; 546/21; 546/22; 548/102; 548/111; 548/112; 548/119; 548/198; 548/233; 548/235; 548/245; 548/311.1; 548/326.5; 548/331.1; 548/364.1; 548/371.4; 556/14; 556/70; 556/64; 564/341; 568/8; 568/13; 568/16; 568/17
[58] Field of Search ............... 564/341; 546/264, 546/266, 267, 268.1, 312, 304, 329, 4, 21, 22; 548/102, 111, 112, 119, 198, 233, 235, 245, 311.1, 326.5, 331.1, 364.1, 371.4; 556/14, 70, 64; 568/8, 13, 16, 17

[56] References Cited

U.S. PATENT DOCUMENTS 4,803,225  2/1989  Dixon et al. .................. 564/341

*Primary Examiner*—Margaret M. Mach

[57] ABSTRACT

The present invention relates particularly to novel preorganized hexadentate ligands that are suitable for completing with a radionuclide, and are useful as general imaging agents for diagnostic purposes.

2 Claims, No Drawings

PREORGANIZED HEXADENTATE LIGANDS USEFUL IN RADIOGRAPHIC IMAGING AGENTS

BACKGROUND OF THE INVENTION

The present invention relates to novel ligands for forming radionuclide complexes, new complexes incorporating such ligands, processes for preparing such complexes, imaging agents incorporating such complexes, and methods of imaging using such imaging agents.

The use of radiographic imaging agents for visualizing skeletal structures, organs, or tissues, is well known in the area of biological and medical research and diagnostic procedures. The procedure whereby such imaging is accomplished, generally involves the preparation of radioactive agents, which, when introduced to the biological subject, are localized in the specific skeletal structures, organs or tissues to be studied. The localized radioactive agents may then be traced, plotted or scintiphotographed by radiation detectors, such as, traversing scanners or scintillation cameras. The distribution and relative intensity of the detected radioactive agents indicates the position of the tissue in which the agent is localized, and also shows the presence of aberrations, pathological conditions or the like.

In general, the radiographic imaging agents comprise radionuclide-labelled compounds; such as complexes of technetium 99 m, rhenium 186 or rhenium 188, or other applicable radionuclides; with appropriate carriers, and auxiliary agents, such as delivery vehicles suitable for injection into, or aspiration by, the patient, physiological buffers and salts, and the like.

DETAILED DESCRIPTION OF THE INVENTION

The present invention relates particularly to novel preorganized hexadentate ligands that are suitable for completing with a radionuclide, and are useful as general imaging agents for diagnostic purposes. In particular the present invention relates to novel ligands having the general formula:

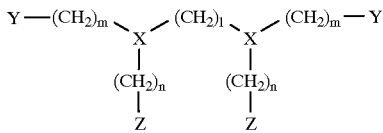

(I)

wherein 1 and m may be the same or different and are from 2 to 5; n is from 2 to 6; X is an N, P, or As atom; Y is selected from the group consisting of

—OH  —SR$^1$  —COOH  —COSH

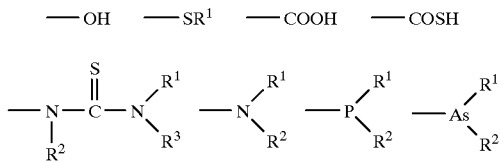

wherein $R_1$–$R^3$ may be the same or different and are selected from the group consisting of hydrogen, alkyl, aryl, hydroxyl, alkoxyl, mono- or poly- hydroxyalkyl, or mono- or poly-alkoxyalkyl; and Z is defined in the same manner as Y above or further may be selected from the group consisting of substituted or unsubstituted

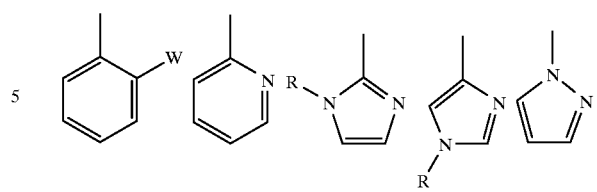

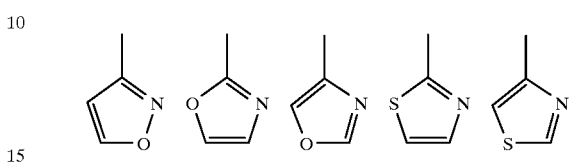

wherein R is defined in the same manner as $R^1$–$R^3$ above, and wherein W is defined in the same manner as Y above. Preferably, Z is selected from either substituted or unsubstituted

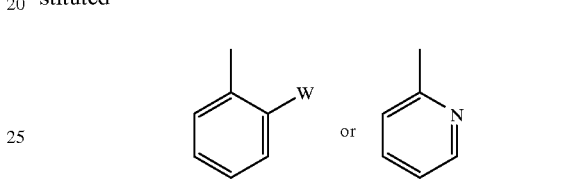

wherein W is defined in the same manner as above.

The novel ligands described above, may be incorporated into radionuclide complexes used as radiographic imaging agents. The complexes of the present invention are prepared by reacting one of the aforementioned ligands with a radionuclide containing solution under radionuclide complex forming reaction conditions. In particular, if a technetium agent is desired, the reaction is carried out with a pertechnetate solution under technetium 99 m complex forming reaction conditions. The solvent may then be removed by any appropriate means, such as evaporation. The complexes are then prepared for administration to the patient by dissolution or suspension in a pharmaceutically acceptable vehicle.

The ligands of the present invention may be prepared from commercially available starting materials such as 2-nitrobenzylbromide, hydroxyethylethylenediamine, etc. by standard synthetic methods as described in the following Examples.

Radionuclide complexes according to the present invention may have the general formula:

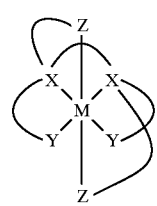

(II)

wherein M is an appropriate radionuclide such as technetium or rhenium, and wherein X, Y, and Z are as defined above in formula (I). The bonds between X—X, and X–Y, may be the same or different and comprise alkyl groups having 2 to 5 carbon atoms; and the bonds between X–Z, may be the same or different and comprise alkyl groups having 2 to 6 carbon atoms. In a preferred embodiment a technetium radionuclide complex having the general formula (II) may be formed from a pertechnetate solution and a ligand having the general formula (I) above, wherein l=2, m=1, n=2, X=N, Y=OH, and wherein Z is substituted or unsubstituted

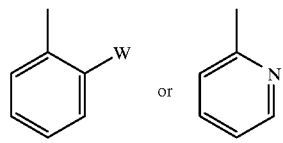

wherein W is

where $R^1$ and $R^2$ are hydrogen.

The radionuclide containing solution may be obtained from radionuclide generators in a known manner. For example, when forming a technetium complex, the pertechnetate solution may be obtained from a technetium generator in a known manner. The radionuclide complex forming reaction is then carried out under appropriate reaction conditions. For example, the technetium 99 m complex forming reaction is carried out under technetium complex forming temperatures, e.g. 20° C. to 100° C. for 10 minutes to several hours. A large excess of the appropriate ligands over the radionuclide complex forming amounts is preferably used. For example, when forming a technetium complex, at least a ten fold excess of the ligands over the pertechnetate solution is used. The pertechnetate is used in technetium complex forming amounts, e.g. about $10^6$ to $10^{12}$ molar amounts.

The present invention also relates to imaging agents containing a radionuclide complex as described above, in an amount sufficient for imaging, together with a pharmaceutically acceptable radiological vehicle. The radiological vehicle should be suitable for injection or aspiration, such as human serum albumin; aqueous buffer solutions, e.g tris (hydromethyl) aminomethane (and its salts), phosphate, citrate, bicarbonate, etc; sterile water; physiological saline; and balanced ionic solutions containing chloride and or dicarbonate salts or normal blood plasma cations such as $Ca^{+2}$, $Na^+$, $K^+$, and $Mg^{+2}$.

The concentration of the imaging agent according to the present invention in the radiological vehicle should be sufficient to provide satisfactory imaging, for example, when using an aqueous solution, the dosage is about 1.0 to 50 millicuries. The imaging agent should be administered so as to remain in the patient for about 1 to 3 hours, although both longer and shorter time periods are acceptable. Therefore, convenient ampules containing 1 to 10 ml of aqueous solution may be prepared.

Imaging may be carried out in the normal manner, for example by injecting a sufficient amount of the imaging composition to provide adequate imaging and then scanning with a suitable machine, such as a gamma camera.

The complexes according to the present invention may be prepared in accordance with the examples set forth below.

EXAMPLE 1

Preparation of N,N'-bis(2-aminobenzyl)-N,N'-bis(2-hydroxyethyl)ethylenediamine

A mixture of 2-nitrobenzylbromide (25 g), N,N'-bis(2-hydroxyethyl)ethylenediamine (8.6 g) and diisopropylethylamine (15 g) in acetonitrile (300 ml) was stirred at room temperature for 4 hours. The reaction mixture diluted with water (700 ml) and extracted with ethyl acetate (3×200 ml). The combined extracts were washed with water (4×200 ml), dried ($Na_2SO_2$), filtered, and the filtrate taken to dryness under reduced pressure to give the desired intermediate as a reddish oil (23 g). This was sufficiently pure to be used in the next step.

The nitro compound (15 g) was dissovled in ethyl acetate (75 ml) and was carefully treated with 10% palladium or carbon catalyst (2 g). The mixture was hydrogenated at 45 psi for 2 hours and filtered through celite. The filtrate was taken to dryness under reduced pressure to yield reddish brown oil. Chromatography on silica (300 g) using chloroform/methanol (9:1) gave the desired ligand (6 g). TLC ($CHCl_3/CH_3OH$, 9:1), single spot ($R_f$ 0.32). $^{13}$C-NMR ($CDCl_3$) δ 146.6, 131.1, 128.8, 123.0, 118.3, 116.2, 59.7, 58.5, 56.2, 52.3.

EXAMPLE 2

A mixture of the ligand prepared in Example 1 above (2 mg) in ethanol (1 ml) was heated with ethanoic $Na^{99m}TcO_4$ and ethanolic $SnCl_2$ (1 mg/ml)(10 ml). The reaction vial was sealed and the mixture heated at 100° C. for 30 minutes. The crude mixture of products were separated by HPLC to give 3 components with the following retention times: peak 1, $R_t$=14.1 min.; peak 2, $R_t$=16.2 min.; and peak 3, $R_t$=22.2 min. All three peaks were stable at least 4 hours and upon dilution with saline solution. Peaks 1 and 2 were neutral complexes, whereas peak 3 was cationic (2 cm/hr) as determined by paper electrophoresis.

What is claimed is:

1. A ligand useful in forming radionuclide complexes, said ligand having the general formula:

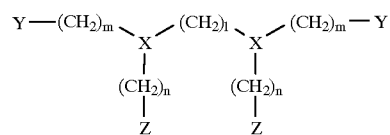

wherein 1 and m may be the same or different and are from 2 to 5; n is from 2 to 6; X is an N, P, or As atom; Y is selected from the group consisting of

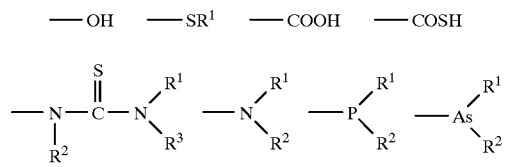

wherein $R^1$–$R^3$ may be the same or different and are selected from the group consisting of hydrogen, alkyl, aryl, hydroxyl, alkoxyl, mono- or polyhydroxyalkyl, or mono- or polyalkoxyalkyl; and Z is defined in the same manner as Y above or further may be selected from the group consisting of

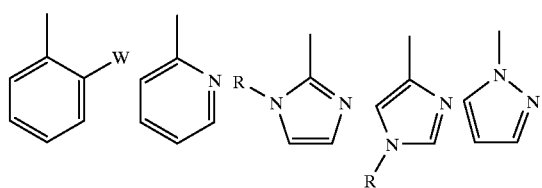
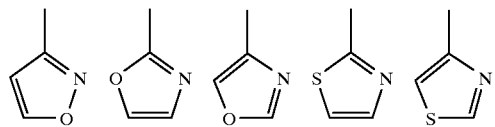
wherein R is defined in the same manner as $R^1$–$R^3$ above, and wherein W is defined in the same manner as Y above.
2. A ligand according to claim 1, wherein Z is selected from the group consisting of
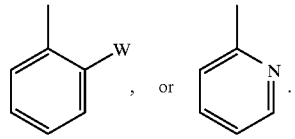
* * * * *